United States Patent [19]

Matsubara et al.

[11] 4,273,932
[45] Jun. 16, 1981

[54] 4-HYDROXY-5,6,7,8-TETRAHYDROQUINOLINE-3-CARBOXYLIC ACIDS AND DERIVATIVES

[75] Inventors: Akira Matsubara, Yokohama; Hideaki Sakai, Fujisawa; Makoto Odate; Takuo Nakano, both of Yokohama, all of Japan

[73] Assignee: Mitsui Toatsu Chemicals, Incorporated, Tokyo, Japan

[21] Appl. No.: 116,560

[22] Filed: Jan. 29, 1980

[30] Foreign Application Priority Data

Mar. 9, 1979 [JP] Japan ................................. 54/26748

[51] Int. Cl.³ ................. C07D 215/56; C07D 499/68; A61K 31/47
[52] U.S. Cl. ................................. 546/156; 260/239.1; 424/258
[58] Field of Search ......................................... 546/156

[56] References Cited

U.S. PATENT DOCUMENTS

| | | | |
|---|---|---|---|
| 3,864,329 | 2/1975 | Tobiki et al. | 546/156 X |
| 3,951,955 | 4/1976 | Tobiki et al. | 260/239.1 |
| 3,992,371 | 11/1976 | Tobiki et al. | 260/239.1 |
| 4,005,075 | 1/1977 | Yamada et al. | 260/239.1 |

FOREIGN PATENT DOCUMENTS

| | | | |
|---|---|---|---|
| 75/49286 | 5/1975 | Japan | 546/156 |
| 79/119484 | 9/1979 | Japan . | |
| 7411324 | 3/1975 | Netherlands | 546/156 |

OTHER PUBLICATIONS

Agui, et al., J. Heterocyclic Chem., 12, pp. 1245–1254 (1975).

Primary Examiner—Donald G. Daus
Assistant Examiner—Diana G. Rivers
Attorney, Agent, or Firm—Fisher, Christen & Sabol

[57] ABSTRACT

Disclosed is a quinoline derivative having the general formula

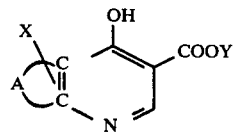

where A represents a six-membered hydrocarbon ring; X represents an oxygen atom, an =NOR$^1$ group in which R$^1$ is a hydrogen atom or a lower alkyl radical of from 1 to 5 carbon atoms, a hydroxyl group, or an —NHR$^2$ group in which R$^2$ is a hydrogen atom or an acyl group; and Y represents a hydrogen atom, a salt-forming radical, or an ester-forming radical. This quinoline derivative is a novel compound which has antiallergic effects in itself and is useful as an intermediate in the production of penicillin or cephalosporin derivatives.

16 Claims, No Drawings

4-HYDROXY-5,6,7,8-TETRAHYDROQUINOLINE-3-CARBOXYLIC ACIDS AND DERIVATIVES

FIELD OF THE INVENTION

This invention relates to quinoline derivatives which have antiallergic effects in themselves and are useful as intermediates in the production of penicillin or cephalosporin derivatives.

BRIEF SUMMARY OF THE INVENTION

It is an object of the present invention to provide a quinoline derivative which has antiallergic effects in itself and is useful as an intermediate in the production of penicillin or cephalosporin derivatives.

According to the present invention, there is provided a quinoline derivative having the general formula

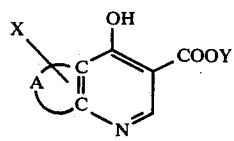 (1)

where A represents a six-membered hydrocarbon ring; X represents an oxygen atom, an $=NOR^1$ group in which $R^1$ is a hydrogen atom or a lower alkyl radical of from 1 to 5 carbon atoms, a hydroxyl group, or an $-NHR^2$ group in which $R^2$ is a hydrogen atom or an acyl group; and Y represents a hydrogen atom, a salt-forming radical, or an ester-forming radical.

DETAILED DESCRIPTION OF THE INVENTION

The quinoline derivatives within the scope of the present invention are novel compounds which have antiallergic effects in themselves and are useful as intermediates in the production of penicillin or cephalosporin derivatives. For example, as described in the Japanese Patent Application Nos. 24956/'78, now Japanese Patent Publication No. 119484/79, published Sept. 17, 1979 and 146055/'78 filed in the name of the Mitsui Toatsu Chemicals, Inc., a variety of penicillin derivatives can be synthesized by reacting a quinoline derivative of the present inventon having a reactive substituent on its carboxyl group with ampicillin. These penicillin derivatives have a wide antimicrobial spectrum and are useful in the treatment of infectious diseases owing to their powerful antibacterial activities against Gram-negative organisms, particularly those of the genus Pseudomonas. Specific examples of these penicillin derivatives include 6-[D-(−)-α-(4-hydroxy-5,6,7,8-tetrahydro-5-oxo-3-quinolinecarboxyamido)-phenylacetamido]penicillanic acid, 6-[D-(−)-α-(4-hydroxy-5-hydroxyimino-5,6,7,8-tetrahydroquinoline-3-carboxyamido)phenylacetamido]penicillanic acid, 6-[D-(−)-α-(5-ethoxyimino-4-hydroxy-5,6,7,8-tetrahydroquinoline-3-carboxyamido)phenylacetamido]-penicillanic acid, 6-[D-(−)-α-(4,5-dihydroxy-5,6,7,8-tetrahydroquinoline-3-carboxyamido)-phenylacetamido]penicillanic acid, 6-[D-(−)-α-(5-acetamido-4-hydroxy-5,6,7,8-tetrahydroquinoline-3-carboxyamido)phenylacetamido]penicillanic acid, and the like.

As has been described previously, the quinoline derivatives within the scope of the present invention have the general formula (1) given above. More specifically, the acyl group represented by $R^2$ is an $R^1CO-$ group in which $R^1$ is a lower alkyl radical of from 1 to 5 carbon atoms. Specific examples of the salt-forming radical represented by Y include inorganic salt-forming radicals derived from sodium, potassium, calcium, etc.; ammonium-forming radicals derived from ammonia, etc.; and organic salt-forming radicals derived from triethylamine, N-methylmorpholine, pyridine, etc. The ester-forming radical represented by Y can be any common radical that combines with the hydroxyl group to form an ester, and specific examples thereof include lower alkyl radicals of from 1 to 5 carbon atoms (which may have one or more halogen, amino, substituted amino, acyloxy, and other substituents) such as methyl, ethyl, propyl, isopropyl, butyl, tert-butyl, etc.; aryl radicals (which may have one or more alkyl, halogen, nitro, amino, substituted amino, aminoalkyl, hydroxy, alkoxy, acyloxy, mercapto, alkylthio, trifluoromethyl, and other substituents) such as phenyl, etc.; aralkyl radicals (which may have one or more alkyl, halogen, nitro, amino, substituted amino, hydroxy, alkoxy, acyloxy, mercapto, alkylthio, trifluoromethyl, and other substituents) such as benzyl, p-methoxybenzyl, etc.; heterocyclic organic radicals such as succinimide, etc.; and the like.

Specific examples of the quinoline derivatives having the general formula (1) include 4-hydroxy-5,6,7,8-tetrahydro-5-oxo-3-quinolinecarboxylic acid, 4-hydroxy-5-hydroxyimino-5,6,7,8-tetrahydroquinoline-3-carboxylic acid, 5-ethoxyimino-4-hydroxy-5,6,7,8-tetrahydroquinoline-3-carboxylic acid, 4,5-dihydroxy-5,6,7,8-tetrahydroquinoline-3-carboxylic acid, and 5-acetamido-4-hydroxy-5,6,7,8-tetrahydroquinoline-3-carboxylic acid; salts of the foregoing carboxylic acids; esters of the foregoing carboxylic acids; and the like.

The quinoline derivatives within the scope of the present invention can be prepared, for example, by the following procedures and by the procedures described in the examples which will be given later.

(1) 3-Amino-2-cyclohexenone is reacted with an ethoxymethylenemalonic acid diester to produce the corresponding N-(3-oxo-1-cyclohexen-1-yl)aminomethylenemalonic acid diester, which is then heated to subject it to ring cleavage and thereby obtain the corresponding 4-hydroxy-5,6,7,8-tetrahydro-5-oxo-3-quinolinecarboxylic acid ester.

(2) In the following procedures, the aforesaid 4-hydroxy-5,6,7,8-tetrahydro-5-oxo-3-quinolinecarboxylic acid ester is used as starting material.

(a) The starting material is hydrolyzed to produce 4-hydroxy-5,6,7,8-tetrahydro-5-oxo-3-quinolinecarboxylic acid.

(b) The starting material is reacted with hydroxylamine hydrochloride ($NH_2OH.HCl$) to produce the corresponding 4-hydroxy-5-hydroxyimino-5,6,7,8-tetrahydroquinoline-3-carboxylic acid ester, which is then hydrolyzed to obtain 4-hydroxy-5-hydroxyimino-5,6,7,8-tetrahydroquinoline-3-carboxylic acid.

(c) The aforesaid intermediate product, 4-hydroxy-5-hydroxyimino-5,6,7,8-tetrahydroquinoline-3-carboxylic acid ester, is reacted with an alkyl iodide ($R^1I$) to produce the corresponding 5-alkyloxyimino-4-hydroxy-5,6,7,8-tetrahydroquinoline-3-carboxylic acid ester, which is then hydrolyzed to obtain 5-alkyloxyimino-4-hydroxy-5,6,7,8-tetrahydroquinoline-3-carboxylic acid.

(3) In the following procedures, the aforesaid 4-hydroxy-5,6,7,8-tetrahydro-5-oxo-3-quinolinecarboxylic acid ester is used as starting material.

(a) The starting material is reacted with zinc in acetic acid (Zn-AcOH) to produce the corresponding 5-amino-4-hydroxy-5,6,7,8-tetrahydroquinoline-3-carboxylic acid ester. This intermediate product is converted into the corresponding 5-acylamino-4-hydroxy-5,6,7,8-tetrahydroquinoline-3-carboxylic acid ester, which is then hydrolyzed to obtain 5-acylamino-4-hydroxy-5,6,7,8-tetrahydroquinoline-3-carboxylic acid.

(b) The starting material is reacted with sodium boron hydride (NaBH$_4$) to produce the corresponding 4,5-dihydroxy-5,6,7,8-tetrahydroquinoline-3-carboxylic acid ester, which is then hydrolyzed to obtain 4,5-dihydroxy-5,6,7,8-tetrahydroquinoline-3-carboxylic acid.

The preparation of the quinoline derivatives within the scope of the present invention is more fully illustrated by the following examples. However, these examples are only illustrative of the practice of the invention and should not be construed to limit the scope of the invention.

EXAMPLE 1

Synthesis of 4-Hydroxy-5,6,7,8-tetrahydro-5-oxo-3-quinolinecarboxylic Acid Ethyl Ester (1) Synthesis of N-(3-Oxo-1-cyclohexen-1-yl)aminomethylenemalonic Acid Diethyl Ester A mixture of 11.1 g of 3-amino-2-cyclohexenone, 24.2 g of ethoxymethylenemalonic acid diethyl ester, and 0.12 g of p-toluenesulfonic acid was heated on an oil bath at 120°–130° C. for 2 hours. Using column chromatography, the reaction product was purified to obtain a yield of 19.8 g of N-(3-oxo-1-cyclohexen-1-yl)aminomethylenemalonic acid diethyl ester in the form of a pale-yellow viscous oil. The n.m.r. spectrum (d$_6$-DMSO, 60Mc, TMS) of this compound had signals at δ values of 1.24 (3H, t, J=7 Hz), 1.26 (3H, t, J=7 Hz), 1.7–2.75 (6H, m), 4.10 (2H, q, J=7 Hz), 4.18 (2H, q, J=7 Hz), 5.75 (H, s), 8.05 (1H, d, J=13.8 Hz), and 10.2 (1H, d, J=13.8 Hz).

(2) Synthesis of 4-Hydroxy-5,6,7,8-tetrahydro-5-oxo-3-quinolinecarboxylic Acid Ethyl Ester Diphenyl ether (20 ml) was heated to 260° C. or above, and a solution of 6.87 g of N-(3-oxo-1-cyclohexen-1-yl)aminomethylenemalonic acid diethyl ester in 5 ml of diphenyl ether was added thereto drop by drop. The resulting reaction mixture was refluxed for 15 minutes. After being allowed to cool, the reaction mixture was poured into 300 ml of n-hexane. The precipitate so formed was separated by filtration and then purified to obtain a yield of 4.37 g of the desired compound in the form of a pale-yellow powder. This compound melted (and decomposed) at 221°–224° C. Its infrared absorption spectrum (KBr tablet) had absorption peaks at 3340, 2960, 1740, 1690, 1635, 1605, 1560, 1510, 1285, 1170, 1150, 1090, 1035, 920 and 815 cm$^{-1}$, and its n.m.r. spectrum (d$_6$-DMSO, 60Mc, TMS) had signals at δ values of 1.31 (3H, t, J=7 Hz), 1.9–3.1 (6H, m), 4.27 (2H, q, J=7 Hz), and 8.55 (1H, s).

EXAMPLE 2

Synthesis of 4-Hydroxy-5,6,7,8-tetrahydro-5-oxo-3-quinolinecarboxylic Acid

To 25 ml of water were added 4.0 g of 4-hydroxy-5,6,7,8-tetrahydro-5-oxo-3-quinolinecarboxylic acid ethyl ester and 2.9 g of sodium hydroxide. The resulting reaction mixture was stirred at 90°–95° C. for 2 hours. After being allowed to cool, the reaction mixture was adjusted to pH 2 with 6 N hydrochloric acid. The crystals so precipitated were separated by filtration, washed with water and ethyl alcohol, and then dried at 120° C. under reduced pressure for 4 hours to obtain a yield of 3.3 g of the desired compound. This compound melted (and decomposed) at 278°–279° C. Its infrared absorption spectrum (KBr tablet) had absorption peaks at 3420, 1740, 1690, 1640, 1500, and 820 cm$^{-1}$.

EXAMPLE 3

Synthesis of 4-Hydroxy-5-hydroxyimino-5,6,7,8-tetrahydroquinoline-3-carboxylic Acid Ethyl Ester To 80 ml of ethyl alcohol were added 2.35 g of 4-hydroxy-5-oxo-5,6,7,8-tetrahydroquinoline-3-carboxylic acid ethyl ester and 0.69 g of hydroxylamine hydrochloride. The resulting reaction mixture was refluxed on an oil bath for 1 hour. After the ethyl alcohol was distilled off under reduced pressure, the residue was dissolved in dilute hydrochloric acid and the resulting solution was adjusted to pH 5.8 with 10% potassium carbonate. The crystals so precipitated were separated by filtration to obtain a yield of 1.8 g of the desired compound. This compound melted (and decomposed) at 245°–247° C. (uncorrected values). Its infrared absorption spectrum (KBr tablet) had absorption peaks at 3240, 3060, 2960, 2920, 1720, 1650, 1550, and 1185 cm$^{-1}$, and its n.m.r. spectrum (CF$_3$COOH, 60Mc, TMS) had signals at δ values of 1.50 (3H, t, J=7.5 Hz), 2.0–2.6 (2H, m), 3.0–3.5 (4H, m), 4.6 (2H, q, J=7.5 Hz), and 8.95 (1H, s).

EXAMPLE 4

Synthesis of 4-Hydroxy-5-hydroxyimino-5,6,7,8-tetrahydroquinoline-3-carboxylic Acid Sodium hydroxide (1 g) was dissolved in 30 ml of water, and 1.5 g of the 4-hydroxy-5-hydroxyimino-5,6,7,8-tetrahydroquinoline-3-carboxylic acid ethyl ester obtained in Example 3 was added thereto. The resulting reaction mixture was stirred on an oil bath at 90° C. for 2 hours. After being cooled, the reaction mixture was adjusted to pH 2.2 with dilute hydrochloric acid. The crystals so precipitated were separated by filtration to obtain a yield of 1.2 g of the desired compound. This compound melted (and decomposed) at 285°–286° C. (uncorrected values). Its infrared absorption spectrum (KBr tablet) had absorption peaks at 3440, 3180, 2880, 1650, 1520, 1400, 1230, 970, and 820 cm$^{-1}$.

EXAMPLE 5

Synthesis of 5-Ethoxyimino-4-hydroxy-5,6,7,8-tetrahydroquinoline-3-carboxylic Acid Ethyl Ester 4-Hydroxy-5-hydroxyimino-5,6,7,8-tetrahydroquinoline-3-carboxylic acid ethyl ester (3.75 g) was suspended in 100 ml of dimethylformamide and then dissolved therein by stirring the suspension on an oil bath at 95° C. Thereafter, 1.04 g of potassium carbonate and then 2.32 g of ethyl iodide were added thereto. The resulting reaction mixture was stirred for 4 hours. After the dimethylformamide was distilled off under reduced pressure, water and ethyl acetate were added to the residue. The organic layer was separated and then stripped of solvent to obtain a yield of 3.0 g of the desired compound. This compound melted at 89°–91° C. (uncorrected values). Its infrared absorption spectrum (KBr tablet) had absorption peaks at 3440, 3000, 2960, 1740, 1640, 1465, 1220, 1190, 1110, 1060, and 990 $cm^{-1}$, and its n.m.r. spectrum (CDCl$_3$, 60Mc, TMS) had signals at $\delta$ values of 1.38 (3H, t, J=6.75 Hz), 1.42 (3H, t, J=7.5 HZ), 1.7–2.2 (2H, m), 2.7–3.15 (4H, m), 4.25 (2H, q. J=6.75 Hz), 4.40 (2H, q, J=7.5 Hz), and 8.77 (1H, s).

EXAMPLE 6

Synthesis of 5-Ethoxyimino-4-hydroxy-5,6,7,8-tetrahydroquinoline-3-carboxylic Acid 5-Ethoxyimino-4-hydroxy-5,6,7,8-tetrahydroquinoline-3-carboxylic acid ethyl ester (2.0 g) was dissolved in a mixture of 20 ml of 1 N sodium hydroxide and 10 ml of ethyl alcohol. The resulting reaction mixture was stirred at 90° C. for 2 hours. Under cooling with ice, the reaction mixture was adjusted to pH 4 with dilute hydrochloric acid. The crystals so precipitated were separated by filtration to obtain a yield of 0.95 g of the desired compound. This compound melted (and decomposed) at 225°–228° C. (uncorrected values). Its infrared absorption spectrum (KBr tablet) had absorption peaks at 3440, 2910, 1690, 1640, 1400, 1060, and 825 $cm^{-1}$, and its n.m.r. spectrum (CF$_3$COOH, 60MC, TMS) had signals at $\delta$ values of 1.57 (3H, t, J=7.5 Hz), 2.0–2.6 (2H, m), 3.0–3.5 (4H, m), 4.59 (2H, q, J=7.5 Hz), and 8.94 (1H, s).

EXAMPLE 7

Synthesis of 4,5-Dihydroxy-5,6,7,8-tetrahydroquinoline-3-carboxylic Acid Ethyl Ester 4-Hydroxy-5,6,7,8-tetrahydro-5-oxo-3-quinolinecarboxylic acid ethyl ester (11.5 g) was suspended in 600 ml of methyl alcohol, and 1.1 g of sodium boron hydride (NaBH$_4$) was added to the suspension with its internal temperature kept at 20°–25° C. After completion of the reaction, the methyl alcohol was distilled off under reduced pressure and 200 ml of water was added to the residue. The resulting solution was adjusted to pH 2.4 with dilute hydrochloric acid and stirred for 30 minutes. Then, under cooling, the solution was adjusted to pH 6.5 with dilute aqueous sodium hydroxide and stirred for 30 minutes. The precipitate so formed was separated by filtration to obtain a yield of 10.4 g of the desired compound. This compound melted at 182°–183° C. (uncorrected values). Its infrared absorption spectrum (KBr tablet) had absorption peaks at 3440, 3160, 2960, 1730, 1655, 1540, 1305, and 1190 $cm^{-1}$, and its n.m.r. spectrum (CF$_3$COOH, 60Mc, TMS) had signals at $\delta$ values of 1.52 (3H, t, J=6.8 Hz), 1.9–2.4 (4H, m), 2.9–3.3 (2H, m), 4.64 (2H, q, J=6.8 Hz), 5.48 (1H, bs), and 8.95 (1H, d, J=6.0 Hz).

EXAMPLE 8

Synthesis of 4,5-Dihydroxy-5,6,7,8-tetrahydroquinoline-3-carboxylic Acid 4,5-Dihydroxy-5,6,7,8-tetrahydroquinoline-3-carboxylic acid ethyl ester (4.7 g) was dissolved in 40 ml of 1 N sodium hydroxide. The resulting solution was stirred on an oil bath at 50° C. for 3 hours and then allowed to stand at room temperature overnight. After the small amount of insoluble matter was removed, the solution was adjusted to pH 2.4 with dilute hydrochloric acid. The precipitate so formed was separated by filtration to obtain a yield of 3.8 g of the desired compound. Its infrared absorption spectrum (KBr tablet) had absorption peaks at 3400, 3060, 2960, 1700, 1650, 1530, and 1510 $cm^{-1}$, and its n.m.r. spectrum (CF$_3$COOH, 60Mc, TMS) had signals at $\delta$ values of 1.8–2.6 (4H, m), 2.9–3.5 (2H, m), 5.55 (1H, bs), and 8.9–9.2 (1H, m).

EXAMPLE 9

Synthesis of 5-Amino-4-hydroxy-5,6,7,8-tetrahydroquinoline-3-carboxylic Acid Ethyl Ester 4-Hydroxy-5,6,7,8-tetrahydro-5-hydroxyimino-3-quinolinecarboxylic acid ethyl ester (2.5 g) was suspended in 90 ml of acetic acid, and 2.6 g of zinc dust was added to the suspension with its internal temperature kept at 60° C. The resulting reaction mixture was stirred for 5 hours. After the reaction mixture was filtered to remove the insoluble matter, the filtrate was concentrated to obtain the desired compound as a crude product. This crude product was used in the succeeding Example 10 without further purification.

EXAMPLE 10

Synthesis of 5-Acetamido-4-hydroxy-5,6,7,8-tetrahydroquinoline-3-carboxylic Acid Ethyl Ester The crude product obtained in Example 9 was dissolved in 150 ml of chloroform, and 7.5 g of acetic anhydride was added thereto. The resulting reaction mixture was allowed to stand overnight. The precipitate so formed was separated by filtration to obtain a yield of 1.1 g of the desired compound. Its n.m.r. spectrum (CF$_3$COOH, 60Mc, TMS) had signals at $\delta$ values of 1.50 (3H, t, J=6.8 Hz), 1.8–2.6 (4H, m), 2.40 (3H, s), 2.9–3.4 (2H, m), 4.65 (2H, d, J=6.8 Hz), 5.65 (1H, d, J=8.3 Hz), 8.40 (1H, d, J=8.3 Hz), and 8.85–9.15 (1H, m).

EXAMPLE 11

Synthesis of 5-Acetamido-4-hydroxy-5,6,7,8-tetrahydroquinoline-3-carboxylic Acid 5-Acetamido-4-hydroxy-5,6,7,8-tetrahydroquinoline-3-carboxylic acid ethyl ester (0.8 g) was suspended in 20 ml of 1 N sodium hydroxide. The resulting reaction mixture was heated on an oil bath at 110° C. for 2 hours. After being cooled, the reaction mixture was filtered to remove the insoluble matter, and the filtrate was adjusted to pH 2.5 with dilute hydrochloric acid. The precipitate so formed was separated by filtration to obtain a yield of 0.4 g of the desired compound. This compound melted (and decomposed) at 285°–287° C. (uncorrected values). Its infrared absorption spectrum (KBr tablet) had absorption peaks at 3420, 3340, 3260, 3080, 2940, 1710, 1650, 1635, 1290, and 810 cm$^{-1}$. and its n.m.r. spectrum (CF$_3$COOH, 60Mc, TMS) had signals at δ values of 1.8–2.6 (4H, m), 2.43 (3H, s), 2.9–3.5 (2H, m), 5.72 (1H, d, J=8.3 Hz), 8.47 (1H, d, J=8.3 Hz), and 9.0–9.3 (1H, m).

What is claimed is:

1. Quinoline derivative having the general formula:

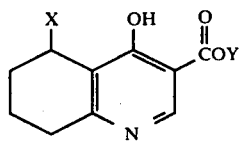

wherein X represents an oxygen atom, an =NOR$^1$ group in which R$^1$ is a hydrogen atom or a lower alkyl radical of from 1 to 5 carbon atoms, a hydroxyl group, or an —NHR$^2$ group in which R$^2$ is either a hydrogen atom or an R$^1$CO— group in which R$^1$ is a lower alkyl radical of from 1 to 5 carbon atoms, and wherein Y represents a hydrogen atom, a lower alkyl radical of from 1 to 5 carbon atoms, or a salt-forming radical selected from the group consisting of inorganic salt-forming radicals and organic salt-forming radicals.

2. A quinoline derivative as claimed in claim 1 wherein said salt-forming radical is derived from the group consisting of sodium, potassium, calcium, ammonia, triethylamine, N-methylmorpholine and pyridine.

3. A quinoline derivative as claimed in claim 1 wherein Y is hydrogen.

4. The quinoline derivative of claim 1 which has the general formula

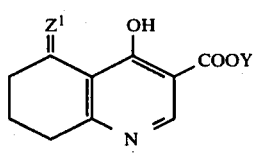

where Z$^1$ represents an oxygen atom or an =NOR$^1$ group in which R$^1$ is a hydrogen atom or a lower alkyl radical of from 1 to 5 carbon atoms; and Y represents a hydrogen atom, a salt-forming radical selected from the group consisting of inorganic salt-forming radicals and organic salt-forming radicals, or a lower alkyl radical of from 1 to 5 carbon atoms.

5. The quinoline derivative of claim 1 which has the general formula

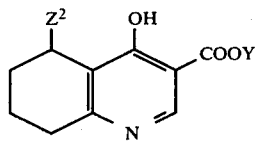

where Z$^2$ is a hydroxyl group or an —NHR$^2$ group in which R$^2$ is a hydrogen atom or an R$^1$CO— group in which R$^1$ is a lower alkyl radical of from 1 to 5 carbon atoms.

6. The quinoline derivative of claim 1 which is 4-hydroxy-5,6,7,8-tetrahydro-5-oxo-3-quinolinecarboxylic acid ethyl ester.

7. The quinoline derivative of claim 1 which is 4-hydroxy-5,6,7,8-tetrahydro-5-oxo-3-quinolinecarboxylic acid.

8. The quinoline derivative of claim 1 which is 4-hydroxy-5-hydroxyimino-5,6,7,8-tetrahydroquinoline-3-carboxylic acid ethyl ester.

9. The quinoline derivative of claim 1 which is 4-hydroxy-5-hydroxyimino-5,6,7,8-tetrahydroquinoline-3-carboxylic acid.

10. The quinoline derivative of claim 1 which is 5-ethoxyimino-4-hydroxy-5,6,7,8-tetrahydroquinoline-3-carboxylic acid ethyl ester.

11. The quinoline derivative of claim 1 which is 5-ethoxyimino-4-hydroxy-5,6,7,8-tetrahydroquinoline-3-carboxylic acid.

12. The quinoline derivative of claim 1 which is 4,5-dihydroxy-5,6,7,8-tetrahydroquinoline-3-carboxylic acid ethyl ester.

13. The quinoline derivative of claim 1 which is 4,5-dihydroxy-5,6,7,8-tetrahydroquinoline-3-carboxylic acid.

14. The quinoline derivative of claim 1 which is 5-amino-4-hydroxy-5,6,7,8-tetrahydroquinoline-3-carboxylic acid ethyl ester.

15. The quinoline derivative of claim 1 which is 5-acetamido-4-hydroxy-5,6,7,8-tetrahydroquinoline-3-carboxylic acid ethyl ester.

16. The quinoline derivative of claim 1 which is 5-acetamido-4-hydroxy-5,6,7,8-tetrahydroquinoline-3-carboxylic acid.

* * * * *